United States Patent
Schaafsma et al.

[11] 3,932,511
[45] Jan. 13, 1976

[54] PREPARATION OF CYCLOHEXANE-1,3-DIONE AND OF ALKYL-SUBSTITUTED DERIVATIVES THEREOF

[75] Inventors: Sijbrandus E. Schaafsma, Beek; Johannes E. L. Claassens, Heerlen; Egidius J. M. Verheijen, Sittard, all of Netherlands

[73] Assignee: Stamicarbon B.V., Geleen, Netherlands

[22] Filed: Mar. 11, 1974

[21] Appl. No.: 450,220

[30] Foreign Application Priority Data
Mar. 14, 1973 Netherlands.................. 7303536

[52] U.S. Cl....... 260/586 C; 260/586 R; 260/617 R; 260/621 R; 260/621 H; 260/624 R; 260/625; 260/631 R; 260/638 R
[51] Int. Cl.²........................................ C07C 45/00
[58] Field of Search.............. 260/586 C

[56] References Cited
UNITED STATES PATENTS
3,595,930  7/1971  Hofmann et al............... 260/586 R

OTHER PUBLICATIONS
Vorländer et al., "Justus Liebigs Annalen", 294:270–1.
Bornstein et al. "Chem. Abstracts", 48:9933e (1954).
Kost et al. "Zhur. Absch. Khim", 32:3983–6 (1962).
Mannich et al. "Ber", Vol. 71, pp. 2090–2091 (1938).

*Primary Examiner*—Norman Morgenstern
*Attorney, Agent, or Firm*—Cushman, Darby & Cushman

[57] ABSTRACT

Process for the preparation of cyclohexane-1,3-diones of the formula

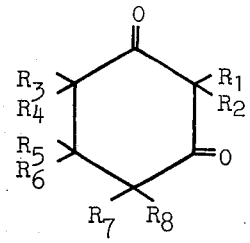

wherein $R_1$–$R_8$, which are the same or different, are each hydrogen or an alkyl group containing up to 6 carbon atoms and the total number of carbon atoms of $R_1$–$R_8$ is not more than 12 carbon atoms, comprising contacting in the gaseous state a delta-keto ester of the formula

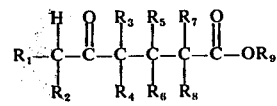

wherein $R_1$–$R_8$ are as defined above and $R_9$ is an alkyl, cycloalkyl, or monocyclic or bicyclic arylalkyl or aryl group containing up to 12 carbon atoms, with a thermally stable solid material having an internal surface area of from about 100 tot 1500 m²/gm. at a temperature of from 100 °C to 500 °C.

10 Claims, No Drawings

PREPARATION OF CYCLOHEXANE-1,3-DIONE AND OF ALKYL-SUBSTITUTED DERIVATIVES THEREOF

The present invention relates to a process for preparing cyclohexane-1,3-dione and the alkyl-substituted derivatives thereof.

It is known from, e.g., the Journal of General Chemistry USSR, volume 32, 1962, pages 3908–3911, that various delta-keto-esters can be cyclized into substituted or unsubstituted cyclohexane-1,3-diones (dihydroresorcinols) by treating the ester with sodium methanolate (sodium methoxide), and neutralizing the resulting alkaline mixture with sulphuric acid, with sodium sulphate obtained as a by-product. At the same time, an alcohol corresponding to the alcohol moiety of the ester group is also obtained.

This known process, however, requires the use of a rather large quantity of sodium methanolate and sulphuric acid, and the resulting sodium sulphate by-product is of little value.

It has now been found that these disadvantages can be avoided and at the same time the desired product can be prepared with a higher yield. In the process according to the present invention for the preparation of cyclohexane-1,3-dione and its alkyl-substituted derivatives, a delta-keto-ester of the general formula:

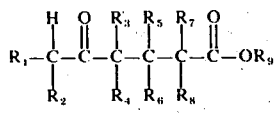

is contacted in the gaseous state at an elevated temperature with a thermally stable solid material having an internal surface area of from about 100–1500 m²/gm. whereby the delta-keto-ester is cyclized with separation of an alcohol corresponding to the alcohol moiety of the ester group, to yield a reaction mixture from which is recovered a cyclohexane-1,3-dione of the general formula

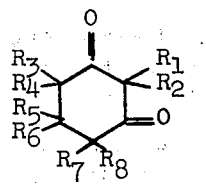

In the above formulas, $R_1$–$R_8$, which are the same or different, each represent, independent of each other, hydrogen or an alkyl group containing up to 6 carbon atoms, the total number of carbon atoms of the substituents $R_1$ to $R_8$ inclusive being at most 12, and $R_9$ represents a hydrocarbon group with at most 12 carbon atoms.

As mentioned above, the process according to the invention also forms an alcohol of the general formula $R_9OH$, in which $R_9$ has the above-mentioned meaning. This alcohol may be recovered as such and re-used for the preparation of additional keto-ester starting material, for instance according to the method referred to in the above-mentioned publication, or according to the method disclosed in U.S. Pat. application, Ser. No. 413,436, filed Nov. 7, 1973, (in which an ester of an alpha-beta-unsaturated carboxylic acid is converted with a ketone into a keto-ester).

The radical $R_9$ can represent various hydrocarbon groups; in particular alkyl-, cycloalkyl-, monocyclic and bicyclic aryl, e.g. phenyl and naphthyl and monocyclic and bicyclic arylalkyl, e.g. benzyl. Groups containing up to 12 carbon atoms are preferred. Especially preferred are lower alkyl groups containing up to 6 carbon atoms, such as methyl, ethyl, n-propyl, isopropyl, n-butyl, sec-butyl, and n-hexyl groups.

When $R_1$–$R_8$ are alkyl, especially preferred are lower alkyl groups containing up to 6 carbon atoms, and in particular, those alkyl groups preferred for $R_9$.

The process according to this invention may be realized at different temperatures above the ambient temperature. In practice, temperatures of between about 100° and about 500°C are preferred. A high efficiency and, at the same time, a sufficiently rapid reaction can be achieved at temperatures between about 200°C and about 350°C.

With regard to the thermally stable solid materials, any material can be used provided that it is thermally stable and causes the delta-keto ester herein defined to cyclize to the desired product without adversely affecting the starting material, product or the course of the reaction. Appropriate materials can be determined by routine experimentation.

Among the solid materials that can be used, active carbon is highly suitable. Other materials that have been found to be effective include magnesium oxide, calcium oxide, barium oxide, strontium oxide and graphite.

Although the internal surface area of the solid material may vary, an area between about 100 to about 1,500 m² per gram is preferred.

Otherwise, the process according to the invention may be conducted in various ways already well known to those skilled in the art. The starting compound may be diluted with an inert gas, such as nitrogen, carbon dioxide, hydrogen and the like. The solid material may be employed either in the form of a fixed bed or a so-called fluid bed. Different space velocities may be used, for instance velocities of between about 0.1 and about 2 g of keto-ester per milliliter of solid material per hour. By cooling the resulting gaseous reaction mixture, a condensate can be obtained from which, by fractional distillation, the desired product and, possibly, nonconverted starting material, can be recovered. Recovery of the desired product by subjecting the condensed reaction mixture to extraction is also possible.

It will be appreciated, of course, by those skilled in the art that because of keto-enol tautomerism some of the products herein obtained will be in the enol form, i.e. a 3-hydroxy-cyclohexen-2-on-1 will be obtained. Further, the product may comprise a keto-enol mixture. Accordingly, although the products described herein are designated as cyclohexane-1,3-diones, it should be understood that where the structural nature of the product permits, the process includes the formation of the corresponding dihydroresorcinols as well.

The final products obtained according to the invention can be used for the preparation of steroids, e.g. as described in Angewandte Chemie, 13, 492–493 (1971). Where the products are obtained as dihydroresorcinols, they can be conveniently dehydrogenated to the corresponding resorcinols, which are useful in the preparation of dyes, adhesives for wood veneers, and resorcinol-formaldehyde resins. Typical dehydrogenation procedures are described in British Patent Specification No. 1,188,387 and U.S. Pat. No. 3,627,833. See also our copending application, Ser. No. 450,219 and filed on even date herewith.

The invention will be elucidated in more detail in the following examples, which should not be construed, however, as limiting the scope of the invention.

EXAMPLE I

A gaseous mixture of hydrogen and methyl 5-oxo-hexanoat was made to descend for 30 hours through a vertical, tubular reactor, 18 mm. in diameter and 400 mm. in length, containing 30 ml. of carbon (carbonized peat) in the form of little bars each having a diameter of 0.9 mm. and a length of 2–3 mm. (bulk density 0.35 g per ml.; internal surface area approximately 800 m$^2$ per g). The temperature of the carbon was kept at 300°–302°C by means of a heating jacket.

The gaseous mixture (10 moles of hydrogen per mole of methyl 5-oxo-hexanoate) had been obtained by evaporation of the liquid methyl ester and admixture of the vapor with hydrogen. The space velocity amounted to 0.11 g of methyl ester per ml. of solid material per hour.

After an operating period of 28 hours, the resulting gas mixture was passed through a collecting vessel which had been cooled to −20°C for 2 hours, whereupon the condensed reaction product was heated to room temperature. The product so obtained (6.6 g) contained, according to a gas-chromatographic analysis, 5.8% by weight of dihydroresorcinol (cyclohexane-1,3-dione), 92.0% by weight of methyl 5-oxo-hexanoate, and a small quantity of methanol. Taking into account the recovered methyl ester, the yield of dihydroresorcinol amounted to 93%.

EXAMPLE II

The experiment described in Example I was repeated using nitrogen as a carrier gas (10 moles of nitrogen per mole of methyl 5-oxo-hexanoate) instead of hydrogen, keeping the temperature of the catalyst at 330°–332°C.

6.5 g of product were obtained which, according to a gas-chromatographic analysis, contained 12.0% by weight of dihydroresorcinol and 84.2% by weight of methyl 5-oxo-hexanoate. Based on the recovered methyl ester, the dihydroresorcinol yield amounted to 96%.

EXAMPLE III

The experiment described in Example II was repeated using ethyl 5-oxo-4-methyl hexanoate as starting material. For every mole of the ethyl ester, 10 moles of nitrogen were used.

After an operating period of eight hours, the gaseous reaction mixture was made to condense for 2 hours in the way described in Example I.

6.6 g of product were obtained which, according to gas-chromatographic analysis, contained 26.4 % by weight of 4-methylcyclohexane-1,3-dione and 62.0 % by weight of ethyl 5-oxo-4-methyl hexanoate.

Based on the quantity of ethyl ester converted, the efficiency amounted to 94 %.

EXAMPLE IV

The experiment described in Example II was repeated using methyl 4-methyl-5-oxo-heptanoate as starting material. For every mole of the ester, 10 moles of nitrogen were used. The tubular reactor contained 20 ml of carbon.

After an operating period of twelve hours, the gaseous reaction mixture was made to condense for 22.8 hours in the way described in Example I.

55.6 g of product were obtained which, according to gas-chromatographic analysis, contained 58.9 % by weight of 2,4-dimethylcyclohexane-1,3-dione and 19.0 % by weight of methyl 4-methyl-5-oxo-heptanoate.

Based on the quantity of methyl ester converted, the efficiency amounted to 82.7 %.

What is claimed is:

1. A process for the preparation of a cyclohexane-1,3-dione of the formula

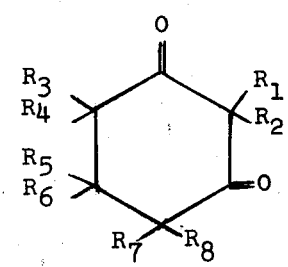

wherein $R_1$–$R_8$, which are the same or different, are each hydrogen or an alkyl group containing up to 6 carbon atoms and the total number of carbon atoms of $R_1$–$R_8$ is not more than 12 carbons which comprises contacting a delta-keto ester of the formula

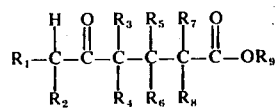

wherein, $R_1$–$R_8$ are as defined above and $R_9$ is an alkyl, cycloalkyl, or monocyclic or bicyclic aryl or arylalkyl group containing up to 12 carbon atoms, in the gaseous state at a temperature from about 100°C to about 500°C with a thermally stable solid material which is active carbon, magnesium oxide, calcium oxide, barium oxide, strontium oxide or graphite and which has an internal surface area of from about 100 to 1,500 m$^2$/gm.

2. The process of claim 1 wherein the temperature is from about 200°C to about 350°C.

3. The process of claim 1 wherein $R_9$ is alkyl of up to 6 carbon atoms.

4. The process of claim 2 wherein the 1,3-dione is cyclohexane-1,3-dione and the delta-keto-ester is a lower alkyl 5-oxo-hexanoate wherein $R_9$ is alkyl of up to 6 carbon atoms.

5. The process of claim 1 wherein the delta-keto ester is diluted with an inert gas.

6. A process for the preparation of a cyclohexane-1,3-dione of the formula

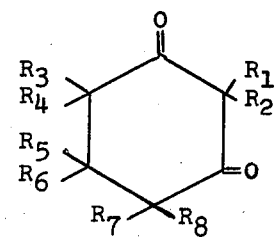

wherein $R_1-R_8$, which are the same or different, are each hydrogen or an alkyl group containing up to 6 carbon atoms and the total number of carbon atoms of $R_1-R_8$ is not more than 12 carbons which comprises contacting a delta-keto ester of the formula

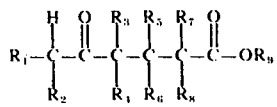

wherein, $R_1-R_8$ are as defined above and $R_9$ is an alkyl, cycloalkyl, or monocyclic or bicyclic aryl or arylalkyl group containing up to 12 carbon atoms, in the gaseous state at a temperature from about 100°C to about 500°C with a thermally stable solid material which is active carbon or magnesium oxide having an internal surface area of from about 100 to 1,500 m²/gm.

7. The process of claim 6 wherein the temperature is from about 200°C to about 350°C and said stable solid material is active carbon.

8. The process of claim 6, wherein $R_9$ is alkyl of up to 6 carbon atoms.

9. The process of claim 7, wherein the 1,3-dione is cyclohexane-1,3-dione and the delta-keto ester is a lower alkyl 5-oxyl-hexanoate, wherein $R_9$ is alkyl of up to 6 carbon atoms.

10. The process of claim 6, wherein the delta-keto ester is diluted with an inert gas.

* * * * *